United States Patent [19]

Currey

[11] Patent Number: 4,764,290

[45] Date of Patent: Aug. 16, 1988

[54] IDENTIFICATION MARKING OF OILS

[75] Inventor: William C. Currey, Houston, Tex.

[73] Assignee: National Identification Laboratories, Inc., Baton Rouge, La.

[21] Appl. No.: 9,662

[22] Filed: Feb. 2, 1987

[51] Int. Cl.$^4$ ........................................... C10M 171/06
[52] U.S. Cl. ......................................... 252/11; 44/59; 252/50
[58] Field of Search ........................ 252/11.50; 44/59

[56] References Cited

U.S. PATENT DOCUMENTS

| | | |
|---|---|---|
| 1,824,977 | 9/1931 | Alleman . |
| 1,969,249 | 8/1934 | Alleman . |
| 1,997,670 | 4/1935 | Armour . |
| 2,046,365 | 7/1936 | Cassidy et al. . |
| 2,265,189 | 12/1941 | Orelup . |
| 2,346,780 | 4/1944 | Orelup . |
| 2,519,868 | 8/1950 | Zehner et al. .................. 252/11 |
| 2,689,171 | 9/1954 | Hager et al. . |
| 3,076,698 | 2/1963 | Orelup ........................... 44/59 |
| 3,476,500 | 11/1969 | Litke ............................. 44/59 |
| 3,494,714 | 2/1970 | Litke . |
| 3,861,886 | 1/1975 | Meloy . |
| 3,862,120 | 1/1975 | Orelup . |
| 4,009,008 | 2/1977 | Orelup . |
| 4,049,383 | 9/1977 | Burton et al. . |
| 4,209,302 | 6/1980 | Orelup . |

Primary Examiner—Jacqueline V. Howard
Attorney, Agent, or Firm—George H. Gerstman; Garrettson Ellis

[57] ABSTRACT

Hydrophilic dye is added to oil for providing identification to the oil. The dye is dispersed in the oil in the form of polymolecular particles less than 1 mm. in diameter, for example, as an emulsion. Accordingly, the sample of oil may be exposed to a polar solvent for the dye particles, to cause the dye particles to dissolve in the polar solvent to exhibit an intensified color, when compared with the particles in the oil.

17 Claims, No Drawings

IDENTIFICATION MARKING OF OILS

BACKGROUND OF THE INVENTION

Oils and gasoline are consumed in great volumes, and thus are often stored in large tanks which are not necessarily well protected by a guard. In view of this, especially when considering the situation of crude oil being stored at wellheads in an isolated area, the problem of theft has been significant for many years.

Numerous proposals have been suggested for ways of marking crude oil, gasoline, or other solvents with a dye, for example Cassidy U.S. Pat. No. 2,046,365, or coded powders as disclosed in Meloy U.S. Pat. No. 3,861,886.

However, disadvantages are found in all of the previously proposed systems. For example, it may well be necessary to remove coded powders from the oil product before using it. Also the identification of the coded powders requires at least a microscope and perhaps other, more complicated machinery. There is always the possibility that other particulate matter could be present in the oil or gasoline, with the result that accurate identification might be difficult.

With respect to dyes, there is the wide perception that it is better for the dye to be substantially invisible while present in the oil or gasoline, being rendered visible by some process of identification. Many of these identification processes are complicated chemical reactions requiring specialized reagents and equipment.

There is a need for an oil or gasoline tagging material which is not readily detectable while residing in the oil, but in which one can demonstrate its presence by an easy detection technique, which can be performed at isolated wellheads and other remote areas.

In accordance with this invention, an oil identification system is provided in which the oil itself may show no apparent trace of the identification system present. However, when it is desired to identify the oil, it can be easily and unambiguously done by the simplest of procedures, requiring no special reagents or equipment, and easily performed in the field or anywhere else.

DESCRIPTION OF THE INVENTION

By this invention, a method is provided for identification of oil, which comprises: adding to the oil a hydrophilic dye in a manner such that the dye is dispersed in the oil in the form of polymolecular particles less than 1 mm. in diameter. Accordingly, a sample of the oil may be exposed to a polar solvent for the dye particles, to cause the dye particles to dissolve in the polar solvent to exhibit an intensified color, when compared with the same particles in the oil.

In other words, a sample of the oil containing the particles appears essentially the same as oil without such particles, because the dye particles are clumped together in the form of typically microscopic particles in which their highly colored characteristic is much less noticeable. However, when one wishes to test an oil for the presence of particles in accordance with this invention, one simply provides a polar solvent such as water or an alcohol to the oil sample. The hydrophilic dye particles break up in the presence of these or another, equivalent polar solvent, to display their color.

Thus, by the simple wetting of a handkerchief or a paper towel in a polar solvent such as an alcohol of 1 to 3 carbon atoms, water, acetone, or any mixture thereof, one may cause color to form by bringing the handkerchief into contact with the oil to be tested. The characteristic color of the dye will appear in a manner which can be quite spectacular, due to its sudden appearance. For example, if one gets some oil that contains the dye particles of this invention on the skin, the water in the skin will ultimately cause the dye to appear, in many embodiments of this invention, coloring the skin with its characteristic color.

A "polar solvent" as used herein is a solvent that is more polar than the oil to be identified, and which causes a hydrophilic dye dispersed in the oil to act as described above.

It is to be understood that the term "oil" is also intended to include not only crude oil, but components thereof including gasoline, kerosene, and other refining fractions. Also, other hydrophobic, organic solvents may be marked in accordance with this invention, all of these materials being intended to be included in the term "oil", as used herein, to describe the material which is provided with identification in accordance with this invention.

The dispersed dye particles may be in the form of an emulsion in the oil to be identified. Alternatively, the dye particles may consist essentially of hydrophilic dye molecules chemically bonded to at least one hydrophobic carbon chain per molecule of at least 6 carbon atoms, preferably being a hydrocarbon chain of about 10 to 30 carbon atoms. This provides the hydrophilic dye molecules with a large, hydrophobic segment, which causes the dye particles to form or remain in the oil by agglomeration of hydrophilic portions of the new dye molecules. The agglomerations of dye molecules apparently become surrounded by the hydrophobic carbon chain portions, causing the particles to be dispersed in stable manner throughout the oil in which they reside in the manner of an emulsion, irrespective of whether such a system is a true emulsion or not.

The particles dispersed in the oil in accordance with this invention may typically be from 0.1 to 200 microns in diameter, generally small enough to be substantially invisible when dispersed in the oil.

When an emulsion of a hydrophilic dye is added to oil to be identified, the dye may be present in a liquid emulsion carrier, which may be any liquid that provides a stable emulsion with the dye, and is effectively miscible with the oil for identification, to permit good dispersion of the dye emulsion particles throughout the oil for identification. Such an emulsion carrier may simply be an oil itself; for example, a mineral oil such as crude oil or a processed fraction thereof including gasoline, kerosene or the like. Additionally, vegetable or animal oils may be used instead, for example soybean oil, corn oil, linseed oil, or olive oil. Liquid animal oils or the like may also be used. Purified solvents such as xylene, benzene, cyclohexane dibutyl ketone, or dihexyl ether may be used as well. There appears to be no particular limitation of the types of emulsion carriers that may be used, as long as they can serve to provide a stable emulsion with the hydrophilic dye, and can be used to convey the dye particles into the oil for identification in such a manner that the dye particles are thoroughly distributed throughout the oil.

Appropriate amounts of a surfactant may be included in the emulsion and emulsion carrier, to assist in stabilizing the emulsion. The science of emulsion stabilization is well developed and well understood by those skilled in the art. A partial list of surfactants that can be used in emulsion systems in accordance with this invention is provided below, the particular choice being governed by such factors as the density or viscosity of oils to be identified, the particular hydrophilic dye to be used, and the characteristics of the particular liquid emulsion carrier.

octylphenoxypoly(ethyleneoxy)ethanol
cetyldimethylethylammonium bromide
dimethylbenzylammonium chloride
dodecyldimethylamine
lauryldimethylamine oxide
magnesium lauryl sulfate One overall preferred surfactant is the first one mentioned on the list above.

Specific dyes which may be used in this invention are identifiable under their generic names and classifications immediately below. Such a list is by no means inclusive of all of the dyes which can be used in this invention.

| Name | Classification |
| --- | --- |
| 1. FD & C Blue #1 | Triphenylmethane |
| 2. FD & C Green #3 | Triphenylmethane |
| 3. FD & C Red #3 | Xanthene |
| 4. FD & C Red #4 | Monoazo |
| 5. FD & C Yellow #5 | Pyrazolone |
| 6. Orange B | Pyrazolone |
| 7. D & C Brown #1 | Diazo |
| 8. D & C Orange #5 | Fluoran |
| 9. D & C Red #19 | Xanthene |
| 10. D & C Violet #2 | Anthraquinone |

The above listed dyes are currently approved for cosmetic use by the U.S. Food and Drug Administration, and thus are deemed safe for contact with human skin.

Preferably, the particle size of the emulsion used in this invention may be from about 0.1 to 100 microns, which can make them small enough to be substantially invisible when dispersed in the oil to be identified.

As an alternative, one may provide identification to oil by adding to the oil a hydrophilic dye in a manner that the dye is dispersed in the oil in the form of polymolecular particles of typically less than 200 microns in diameter, where most of the molecules of the hydrophilic dye are each chemically bonded to at least one hydrophobic carbon chain per molecule of at least 6 carbon atoms and preferably about 10 to 30 carbon atoms. Hydrocarbon chains may be used, or, alternatively, carbon chains which contain other substituents in small amounts insufficient to eliminate the hydrophobic characteristic of the carbon chain. For example, oxygen may be present in small amounts as an ether linkage, a hydroxyl group, a carboxyl group, or the like. The resulting materials exhibit surfactant-like properties in their own right, having a hydrophilic dye portion of the molecule, and also at least one long, hydrophobic side chain.

These materials may be made by reacting dyes that have reactable groups such as amine, carboxyl, hydroxyl, or other groups with a reactant that carries a long, hydrophobic carbon chain. For example, a higher fatty acid may be reacted with an amino group on a dye molecule to form a combined, single molecule through an amide linkage. Other reactions for joining a hydrophilic dye molecule and a long hydrophobic carbon chain are readily apparent to those skilled in the art.

The above disclosure and the examples below have been offered for illustrative purposes only, and are not intended to limit the scope of the invention of this application, which is as defined in the claims below.

EXAMPLE I

FD&C #3 red dye was emulsified in soybean oil to form a 16 percent emulsion. In this particular instance no surfactant is needed to provide a stable emulsion. The emulsion formed has a particle size of less than 100 microns.

To 360 barrels of 43.6% gravity crude oil in a tank, ten gallons of the above described emulsion was added. After 20 minutes of waiting without agitation of the oil, to give the emulsion an opportunity to spread throughout the tank, middle and bottom tank samples of crude oil were drawn. Then, a paper hankerchief was wetted with isopropyl alcohol and dipped into each sample. Almost immediately a bright red color appeared on the paper handkerchief, showing that emulsion particles had migrated throughout the tank during the 20 minute period without any agitation.

If, however, there is a need to agitate a given tank of oil to obtain good results after adding dye particles in accordance with this invention, one can easily do it simply by placing some dry ice into the tank, whereby circulation takes place throughout the oil by the rising carbon dioxide bubbles.

It was later found that 2 gallons of the specific emulsion described above was adequate to treat 360 barrels of oil in such a manner that a red indicator color can be easily elicited by the test technique described above.

The treated oil, containing the emulsion of this invention, looks identical to corresponding but untreated oil.

EXAMPLE 2

To 454 grams of stearic acid was added slightly over 501 grams of anthrosene yellow dye (D&C orange #11), enough to provide one molecule of the dye per two molecules of stearic acid. The mixture is dissolved in chloroform and heated with stirring until the solution is homogenous, which takes about an hour or more. The final product is cooled to about 10 degrees C., resulting in the precipitation of the reaction product between the D&C orange #11 and stearic acid, with stearic acid groups being chemically bonded to the larger dye molecule. In this particular instance, two stearic acid groups appear to be bonded to each dye molecule, on the average.

An emulsion of the above reaction product of the dye and stearic acid was made, containing 5% of the diestearate and 95% of crude oil (expressed in weight/volume). Such a product forms a stable emulsion in which the diestearate molecules are uniformly distributed throughout the crude oil. Five gallons of said emulsion may be added to about 360 barrels of crude oil in a tank, to provide oil marking characteristics similar to Example 1, while being substantially invisible in the crude oil.

EXAMPLE 3

When a mixture of 5% FD&C blue #1 dye (triphenylmethane type), 1% of octylphenoxypoly(ethyleneoxy)ethanol, and 94% of crude oil (weight/volume) is prepared, vigorous stirring of the mixture results in a stable emulsion. This emulsion may be used in a manner similar to the previous example to mark crude oil. Alternatively, it may also be used to mark gasoline, kerosene, or purified organic solvents such as toluene or cyclohexane.

The emulsion used in Example 1 is particularly suitable for normal viscosity crude oil.

The emulsion of Example 2 is more hydrophobic in nature, and thus may be useful for marking oil that is being transported across a body of water in a tanker, since it will not readily leach out of the oil into the water in the event of an oil spill. The identification of the oil may preferably be done in Example 2 by using chloroform as the polar solvent for the dye particles. It causes the dye particles to quickly dissolve, to exhibit the customary, intensified color, when compared with the same particles in the oil.

The emulsion of Example 3 may be used with crude oil of very high viscosity. The presence of the surfactant helps to disperse the dye in the crude oil.

The marker of this invention may be used in gasoline without interfering seriously with its use in most internal combustion engines. Similarly, the marker may be used in refined oils and other products without serious degradation of the product quality. Crude oil marked with the marker of this invention may have it removed during refining.

That which is claimed is:

1. The method of providing identification to oil, which comprises: adding to said oil a hydrophilic dye in a manner and concentration such that the dye is dispersed in the oil in the form of polymolecular particles less than 1 mm. in diameter and the color of the oil is substantially unchanged, said concentration being sufficient whereby a sample of said oil may be exposed to a polar solvent for said dye particles, to cause said dye particles to dissolve in said polar solvent to exhibit a perceptible, intensified color, when compared with the same particles in the oil.

2. The method of claim 1 in which said particles are from 0.1 to 200 microns in diameter.

3. The method of claim 1 in which said dye particles are small enough to be substantially invisible when dispersed in said oil.

4. The method of claim 1 in which said dye particles are in the form of an emulsion in said oil.

5. The method of claim 1 in which said polar solvent is water or an alcohol of no more than three carbon atoms.

6. The method of claim 1 including the step of identifying the presence of said dye in the oil by wetting a piece of fibrous material with a polar solvent for said dye particles and adding a sample of said oil and dispersed particles to said fibrous material, whereby said dye particles reveal their color more strongly.

7. The method of providing identification to oil, which comprises: adding to said oil an emulsion of a hydrophilic dye in a liquid emulsion carrier that is substantially miscible with the oil to which it is added, to cause the hydrophilic dye emulsion to be dispersed throughout said oil, the concentration of such emulsion in the oil being insufficient to substantially change the color of the oil but sufficient whereby a sample of said oil may be exposed to a polar solvent for said dye to cause said dye particles to dissolve in said polar solvent to exhibit a perceptible, intensified color, when compared with the same particles in the oil.

8. The method of claim 7 in which said particles are from 0.1 to 100 microns in diameter.

9. The method of claim 7 in which said dye emulsion consists essentially of dye particles small enough to be substantially invisible when dispersed in said oil.

10. The method of claim 7 in which said polar solvent is an alcohol of 1 to 3 carbon atoms.

11. The method of identifying the presence of a dye in oil where said dye is dispersed in the oil in the form of polymolecular particles less than 1 mm. in diameter, which method comprises exposing a sample of said oil to a polar solvent for said dye particles, to cause said dye particles to dissolve in said polar solvent to exhibit a perceptible, intensified color, when compared with the same particles in the oil.

12. The method of claim 11 in which said particles are from 0.1 to 200 microns in diameter.

13. The method of claim 11 in which said dye particles are in the form of an emulsion in said oil.

14. The method of claim 11 in which said polar solvent is water or an alcohol of no more than 3 carbon atoms.

15. The method of claim 11 in which the presence of dye in the oil is identified by wetting a piece of fibrous material with a polar solvent for said dye particles and adding a sample of said oil and dispersed dye particles to said fibrous material, whereby said dye particles reveal their color more strongly.

16. The method of claim 11 in which said dye particles are in the form of an emulsion in said oil and are from 0.1 to 200 microns in diameter, and the presence of said dye in the oil is identified by wetting a piece of fibrous material with a polar solvent for said dye particles and adding a sample of said oil and dispersed dye particles to the fibrous material, whereby said dye particles reveal their color more strongly.

17. The method of claim 7 including the step of identifying the presence of said dye in the oil by wetting a piece of fibrous material with a polar solvent for said dye particles and adding a sample of said oil and dispersed particles to said fibrous material, whereby said dye particles reveal their color more strongly.

* * * * *